United States Patent
Lochmann et al.

(10) Patent No.: US 12,121,613 B2
(45) Date of Patent: Oct. 22, 2024

(54) LIPOPHILIC TRANSPORT PARTICLES FOR COSMETIC OR PHARMACEUTICAL ACTIVE INGREDIENTS

(71) Applicant: IOI OLEO GMBH, Hamburg (DE)

(72) Inventors: Dirk Lochmann, Deutschland (DE); Sebastian Reyer, Deutschland (DE); Sharareh Salar Behzadi, Osterreich (AT); Michael Stehr, Deutschland (DE); Andreas Zimmer, Osterreich (DE)

(73) Assignee: IOI OLEO GMBH, Hamburg (DE)

( * ) Notice: Subject to any disclaimer, the term of this patent is extended or adjusted under 35 U.S.C. 154(b) by 88 days.

(21) Appl. No.: 17/277,825

(22) PCT Filed: Jul. 1, 2019

(86) PCT No.: PCT/DE2019/000171
§ 371 (c)(1),
(2) Date: Mar. 19, 2021

(87) PCT Pub. No.: WO2020/083413
PCT Pub. Date: Apr. 30, 2020

(65) Prior Publication Data
US 2021/0361577 A1    Nov. 25, 2021

(30) Foreign Application Priority Data

Oct. 22, 2018   (WO) ................ PCT/DE2018/000302
Dec. 11, 2018   (WO) ................ PCT/DE2018/000363
Apr. 30, 2019   (WO) ................ PCT/DE2019/000115

(51) Int. Cl.
*A61K 9/20*    (2006.01)
*A61K 8/02*    (2006.01)
(Continued)

(52) U.S. Cl.
CPC .......... *A61K 9/2054* (2013.01); *A61K 8/0245* (2013.01); *A61K 8/375* (2013.01);
(Continued)

(58) Field of Classification Search
CPC ................ A61K 9/2054; A61K 9/0075; A61K 9/1617; A61K 9/1694; A61K 9/2013;
(Continued)

(56) References Cited

U.S. PATENT DOCUMENTS 4,755,387 A   7/1988   Tzeghai et al.
5,891,476 A   4/1999   Reo et al.
(Continued)

FOREIGN PATENT DOCUMENTS

EP    0368247 A2    5/1990
EP    0514008 A1    11/1992
(Continued)

OTHER PUBLICATIONS

Akiyama, Y., Yoshioka, M., Horibe, H., Hirai, S., Kitamori, N., & Toguchi, H. (1993). Novel oral controlled-release microspheres using polyglycerol esters of fatty acids. Journal of controlled release, 26(1), 1-10. (Year: 1993).*
International Search Report and Written Opinion dated Feb. 21, 2020 in corresponding International Application No. PCT/DE2019/000171.
(Continued)

*Primary Examiner* — Frederick F Krass
*Assistant Examiner* — Lucy M Tien
(74) *Attorney, Agent, or Firm* — Miles & Stockbridge PC; Ajay A. Jagtiani

(57) ABSTRACT

The invention relates to lipophilic transport particles for cosmetic or pharmaceutical active ingredients. The lipophilic transport particles comprise polyglycerol fatty acid ester as a main constituent and, because of the absence of (Continued)

Figure 1:
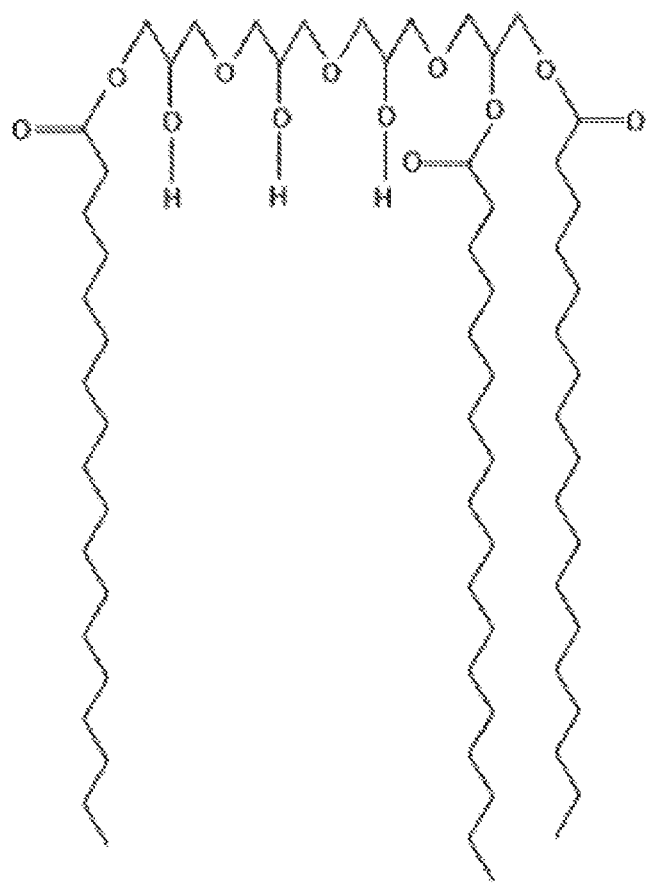
Figure 2:
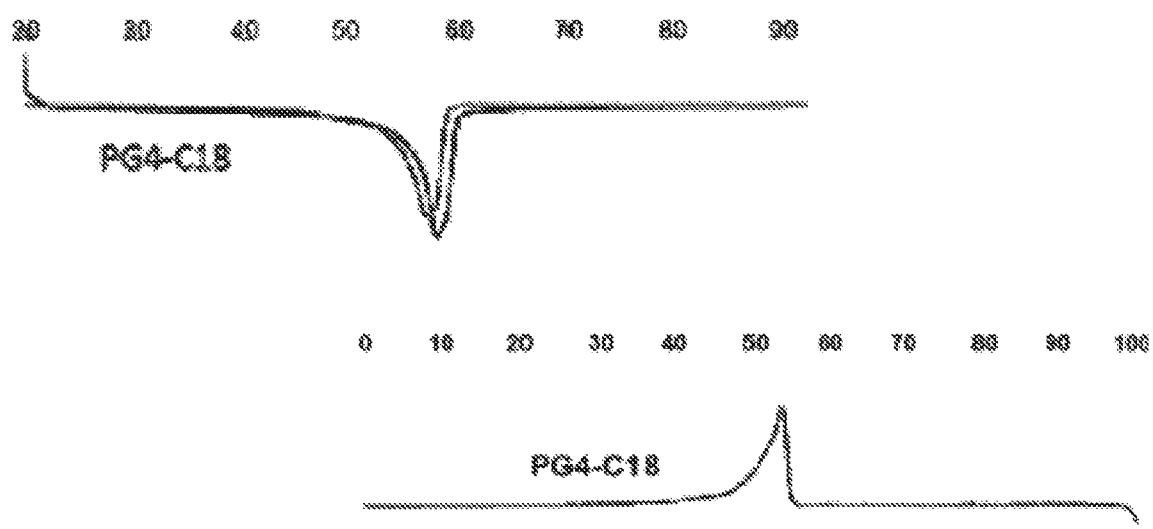
Figure 3:
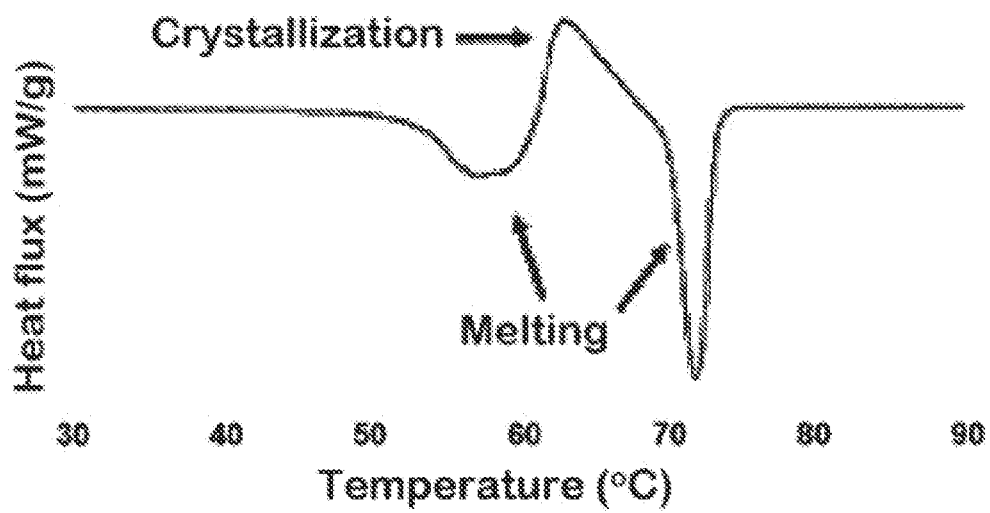
Figure 4:
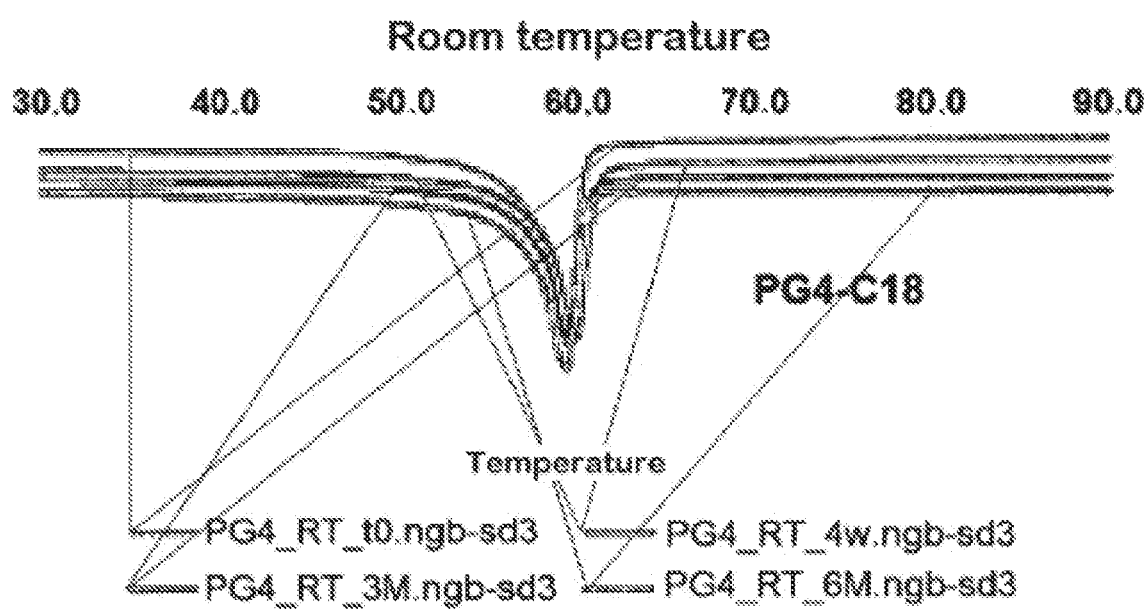
Figure 5:
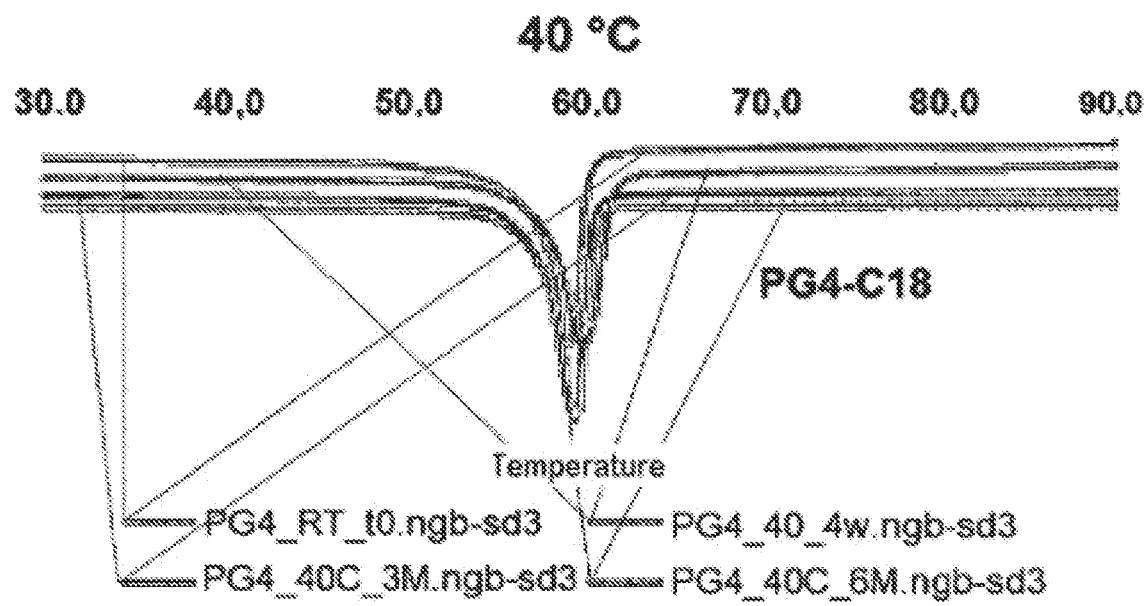
Figure 6:
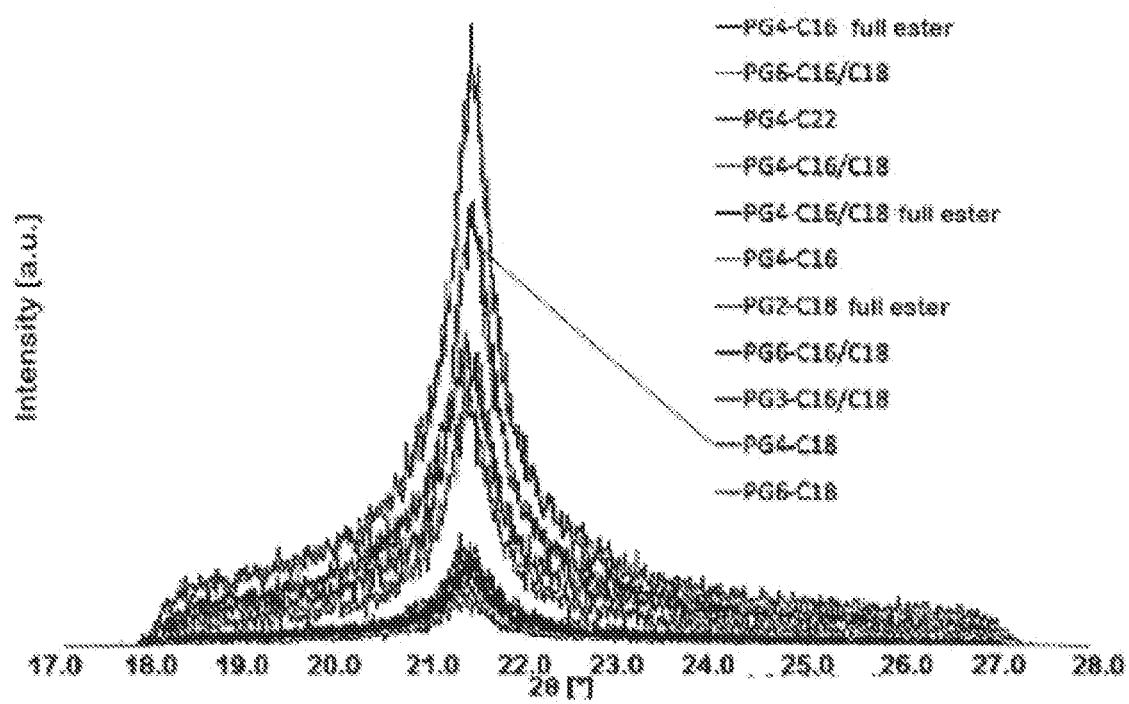
Figure 7:
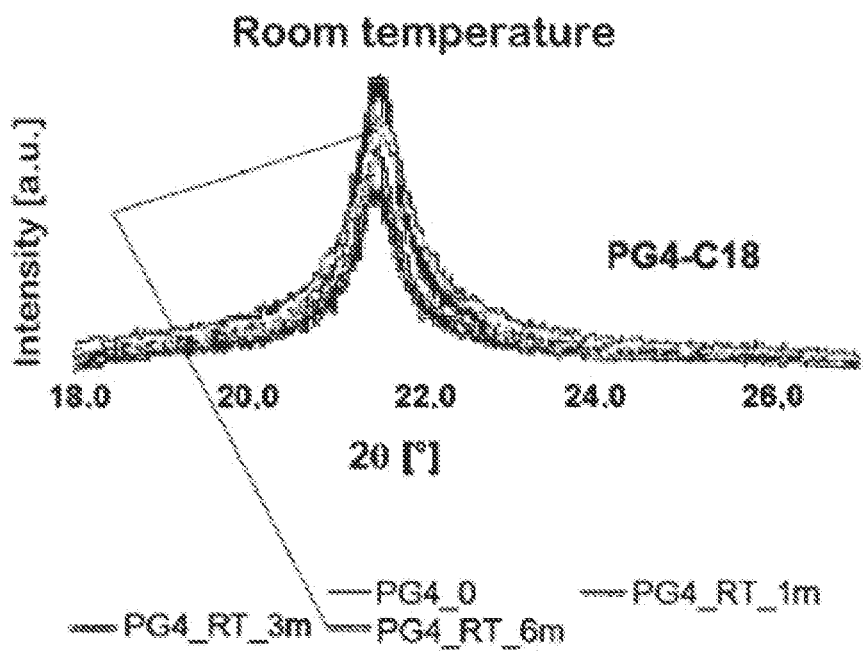
Figure 8:
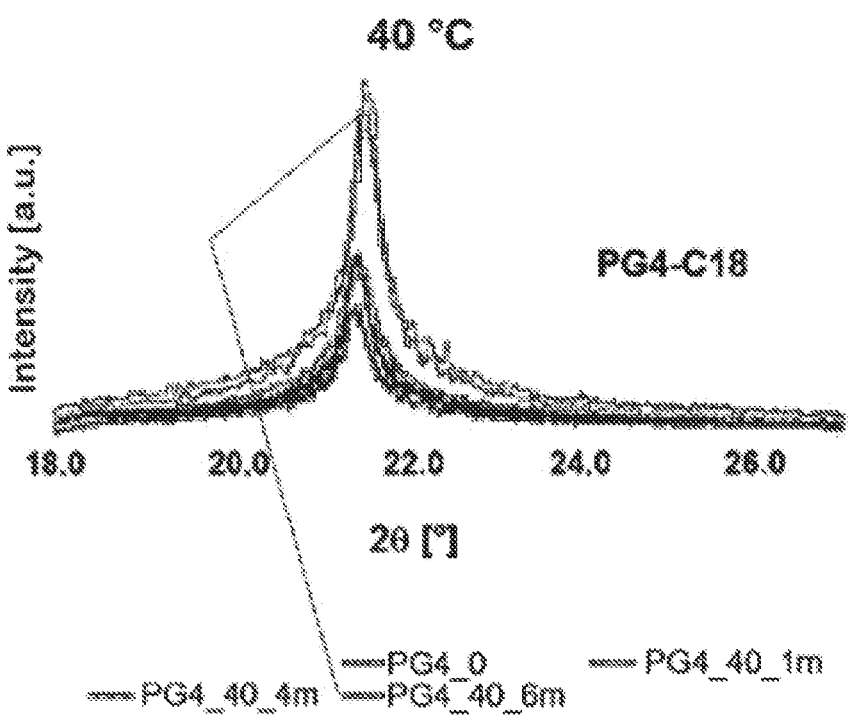
Figure 9:
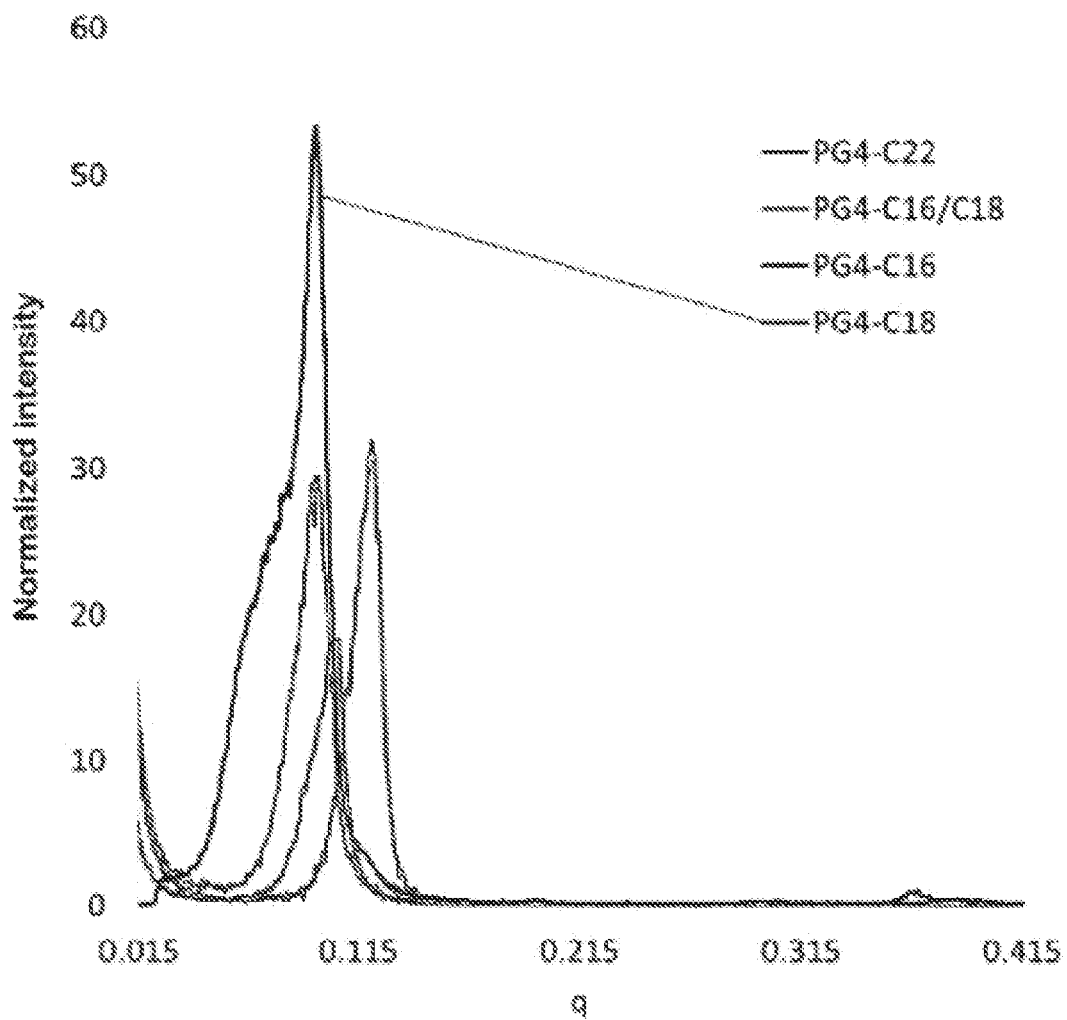
Figure 10:
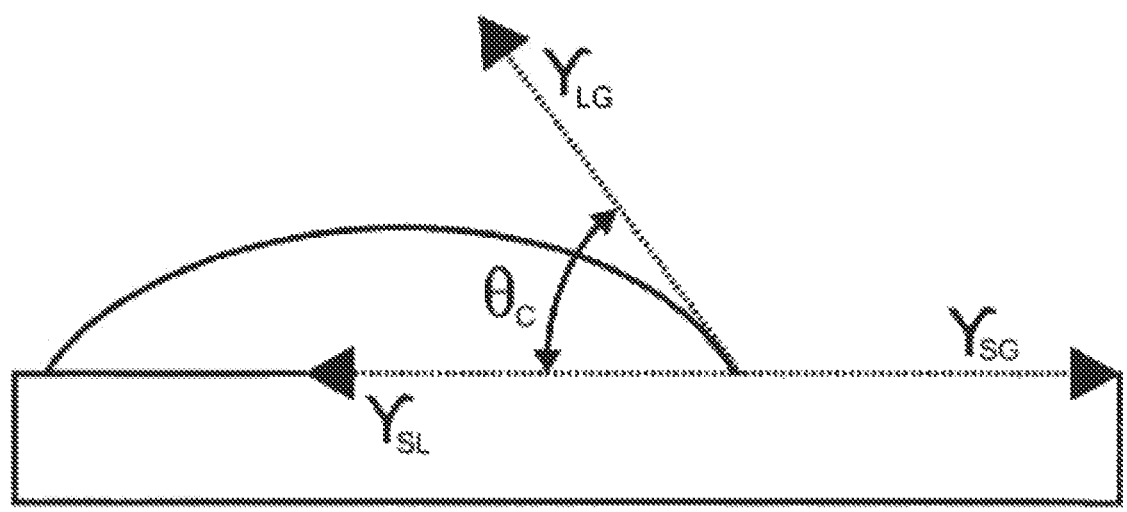

polymorphic transformations, even during long storage, neither have volume changes nor allow the problem of expulsion of the adhering or enclosed active ingredient, due to intense structuring of the crystal lattice and associated compaction, to arise, and therefore the degree of loading with active ingredient and the release profile are stable.

23 Claims, 6 Drawing Sheets

(51) Int. Cl.
    *A61K 8/37*     (2006.01)
    *A61K 9/00*     (2006.01)
    *A61K 9/16*     (2006.01)
    *A61K 31/155*     (2006.01)

(52) U.S. Cl.
    CPC .......... *A61K 9/0075* (2013.01); *A61K 9/1617* (2013.01); *A61K 9/1694* (2013.01); *A61K 9/2013* (2013.01); *A61K 9/2095* (2013.01); *A61K 31/155* (2013.01)

(58) Field of Classification Search
    CPC .... A61K 9/2095; A61K 8/0245; A61K 8/375; A61K 31/155; A61K 47/14
    USPC ........................................................ 424/502
    See application file for complete search history.

(56) References Cited

U.S. PATENT DOCUMENTS

| | | | |
|---|---|---|---|
| 2002/0090345 A1* | 7/2002 | Baichwal | A61K 9/0075 514/60 |
| 2007/0098843 A1* | 5/2007 | Tomohira | A61K 9/1652 426/5 |
| 2010/0004473 A1 | 1/2010 | Kanaya et al. | |
| 2013/0213398 A1* | 8/2013 | Lipp | A61K 9/0073 514/230.2 |
| 2020/0108033 A1* | 4/2020 | Clements | A61K 31/427 |

FOREIGN PATENT DOCUMENTS

| | | |
|---|---|---|
| WO | 2011110926 A1 | 9/2011 |
| WO | 2013183062 A2 | 12/2013 |

OTHER PUBLICATIONS

Akiyama, Y. et al., "Novel Oral Controlled-Release Microspheres Using Polyglycerol Esters of Fatty Acids," Journal of Controlled Release, Elsevier, Amsterdam, NL, vol. 26, No. 1, Jul. 1, 1993, pp. 1-10.

Becker, Karin et al., "Solvent-Free Melting Techniques for the Preparation of Lipid-Based Solid Oral Formulations," Pharmaceutical Research Springer NY, US, vol. 32, No. 5, Mar. 19, 2015, pp. 1519-1545.

Aoshima, H. et al., "Glycerin Fatty Acid Esters as a New Lubricant of Tablets," International Journal of Pharmaceutics, Elsevier, NL, vol. 293, No. 1-2, Apr. 11, 2005, pp. 25-34.

Jaspart, S. et al., "Solid Lipid Microparticles: Formulation, Preparation, Characterisation, Drug Release and Applications," Expert Opinion on Drug Delivery, Informa Healthcare, GB, vol. 2, No. 1, Jan. 1, 2005, pp. 75-87.

Silva, L.F., et al., "Preparation and Characterization of Quercetin-Loaded Solid Lipid Microparticles for Pulmonary Delivery," Powder Technology—Electrostatic Phenomena in Particulate Processes, vol. 239, Feb. 1, 2013, pp. 183-192.

Sanna, V. et al., Preparation and in Vivo Toxicity Study of Solid Lipid Microparticles as Carrier for Pulmonary Administration, AAPS Pharmscitech, vol. 5. No. 2, Jun. 1, 2004, pp. 17-23.

Yohko, A. et al., "Mechanism of Drug Release From Polyglycerol Ester of Fatty Acid-Based Microspheres," Journal of Controlled Release, Elsevier Amsterdam, NL, vol. 27, No. 1, Oct. 1, 1993, pp. 37-45.

Patlolla, R.R. et al., "Formulation, Characterization and Pulmonary Deposition of Nebulized Celecoxib Encapsulated Nanostructured Lipid Carriers," Journal of Controlled Release, vol. 144, No. 2, Jun. 1, 2010, pp. 233-241.

Chiraz, J.M., et al., "Beclomethasone-Loaded Lipidic Nanocarriers for Pulmonary Drug Delivery: Preparation, Characterization and in Vitro Drug Release," Journal of Nanoscience and Nanotechnology, American Scientific Publishers, US, vol. 11, No. 3, Feb. 28, 2011, pp. 1841-1851.

Mehta, P. "Imagine the Superiority of Dry Powder Inhalers From Carrier Engineering," Journal of Drug Delivery, vol. 2018, Jan. 14, 2018, pp. 1-19.

Lopes, D.G., et al. "Role of Lipid Blooming and Crystallite Size in the Performance of Highly Soluable Drug-Loaded Microcapsules," J. Pharm Sci. Vol. 104, No. 12, Dec. 2015, p. 1.

* cited by examiner

LIPOPHILIC TRANSPORT PARTICLES FOR COSMETIC OR PHARMACEUTICAL ACTIVE INGREDIENTS

CROSS-REFERENCE TO RELATED APPLICATIONS

This application is a National Stage of International Application No. PCT/DE2019/000171 filed on Jul. 1, 2019, which is hereby incorporated by reference in its entirety.

The invention relates to lipophilic carrier particles for cosmetic or pharmaceutical active ingredients, which comprise polyglycerol fatty acid esters as the major component and, because of the absence of polymorphic transformations even upon lengthy storage, neither variations in volume, nor the problem of ejection of the adhered or encapsulated active ingredient due to a stronger structuring of the crystal lattice and an associated compaction occur, so that the active ingredient load and release profile are stable.

Inhalation preparations for pulmonary application of pharmaceutical active ingredients have a number of advantages. On the one hand, diseases involving the airways can be treated specifically with them, and on the other hand, if the dimensions of the pharmaceutical-transporting particles are small enough, active ingredients which would not be able to withstand passage through the digestive tract without damage, and thus are usually administered intravenously, can be administered via the lungs with comparative effectiveness, with the advantage of an enhanced compliance with therapy from the viewpoint of the patients to be treated. In order to be able to administer a pharmaceutical active ingredient effectively via the lungs, it should preferably be inhaled in the form of particles with a mass median aerodynamic diameter of between 1 µm and 5 µm. This does not in fact correspond to the size which would be expected for transport deep into the lungs and the alveoli, because smaller particles give rise to the problem that they are conveyed out of the lungs in the exhaled airflow before the pharmaceutical active ingredient can dissociate and be absorbed. In contrast, larger particles generally cannot penetrate deeply enough into the lungs.

In order to prepare particles which can effectively transport the pharmaceutical active ingredients into the lungs, in principle, hydrophilic or lipophilic particles may be used. The use of sugars is widespread, such as a-lactose monohydrate, cyclodextrins, mannitol, dextrose monohydrate, for example, and also metallic stearates such as calcium, magnesium or zinc stearate, or amino acids such as leucine or trileucine (Piyush Mehta, "Imagine the Superiority of Dry Powder Inhalers from Carrier Engineering", Journal of Drug Delivery, Volume 2018, Article ID 5635010, 14 Jan. 2018). The requirements placed on carrier particles are manifold, in particular a high encapsulation efficiency for the active ingredients to be carried, good surface properties, reproducibility, low toxicity, good release properties and disintegration at the target site or low hygroscopicity with a view to good stability upon storage in the inhalation device. In the case of hygroscopicity, stability on storage, reproducibility and take-up capacity, lipophilic carrier particles have good properties, but suffer from the disadvantage that lipids or even triglycerides have a tendency towards polymorphic transformation, and therefore their surface properties can change during storage. A volume increase effect known as "blooming", due to polymorphic transformation, must never be allowed to occur with lipophilic carrier particles for pulmonary application, because the serious volume variations which would be brought about would preclude its use in therapeutics or diagnostics. In addition, a polymorphic transformation would lead to a more structured and more compact crystal lattice configuration which would result in ejecting the adhered or encapsulated active ingredient and thus the controllability of the active ingredient load and of the release profile would be compromised. An unwelcome effect known as the "burst effect" would be likely upon release, during which unpredictable quantities of the active ingredient would suddenly be released. But even for other areas of application of micronized carrier particles such as, for example, in dermal or transdermal applications of cosmetic or pharmaceutical active ingredients, the appearance of polymorphic transformations would negate all the advantages of such lipophilic carrier particles.

Thus, the objective is to provide lipophilic carrier particles for cosmetic or pharmaceutical active ingredients which are in a stable crystalline modification and are also suitable for a pulmonary active ingredient application.

The objective can be achieved by means of such carrier particles which contain one or more polyglycerol fatty acid esters.

Surprisingly, for the first time it has been able to be shown that carrier particles which contain polyglycerol fatty acid esters, abbreviated to PGFEs, as the major component in accordance with claim 1, can be used for the preparation of morphologically stable, lipophilic carrier particles which can be applied via the lungs, when those PGFEs are used which each can be obtained from a complete or partial esterification of a linear or branched polyglycerol containing two to eight glyceryl units with one or more fatty acids respectively containing 6 to 22 carbon atoms.

The simplest polyglycerols which can form the starting materials for an expedient esterification are linear and branched diglycerols with the empirical formula $C_6O_5H_{14}$, which can be synthesized on an industrial scale and in a known manner, for example by reacting glycerol with 2,3-epoxy-1-propanol under basic catalysis with the formation of ether bonds, or by thermal condensation under base catalysis, wherein the fraction containing mainly diglycerols can subsequently be separated.

Diglycerols can occur in three different structurally isomeric forms, namely in the linear form, in which the ether bridge is formed between the respective first carbon atoms of the two glycerol molecules involved, in the branched form, in which the ether bridge is formed between the first carbon atom of the first and the second carbon atom of the second glycerol molecule employed, and in a nucleodendrimeric form, in which the ether bridge is formed between the respective second carbon atoms. In the case of the condensation of two glycerol molecules catalysed by an alkali, up to approximately 80% occurs in the linear form and up to approximately 20% in the branched form, while only a very small quantity of the nucleodendrimeric form is produced.

In the case of esterification with fatty acids, polyglycerols containing more than two glyceryl units may also be used. In general, the polyglycerols are abbreviated to "PG" and an integer n is added as a suffix, which provides the number of polyglyceryl units, i.e. "$PG_n$". As an example, triglycerols are written as $PG_3$ and have the empirical formula $C_9O_7H_{20}$. Complete esterification with a fatty acid, for example with stearic acid, should now take place at all of the free hydroxyl groups of the $PG_n$ molecule. In the case of a linear $PG_3$, then this would take place at the first and second carbon atoms of the first glyceryl unit, at the second carbon atom of the second glyceryl unit and at the second and third carbon atoms of the third glyceryl unit. The empirical formula for this example is therefore given as $C_9O_7H_{15}R_5$, wherein each R represents a fatty acid residue, in the selected example with the empirical formula $C_{18}OH_{35}$.

However, the established abbreviation for polyglycerols esterified with saturated unbranched fatty acids is the designation PG(n)-Cm full ester or, as appropriate, PG(n)-Cm partial ester, wherein the "n" in parentheses, in similar manner to the designation for the polyglycerols, gives the number of glyceryl units contained in the molecule and m represents the number of carbon atoms of the saturated fatty acid used for the esterification reaction. Thus, the "n" represents the number of glyceryl units with the empirical formula $C_3O_2H_5R$ or $C_3O_3H_5R_2$ for marginal glyceryl units, wherein R may represent a fatty acid residue or the hydrogen atom of a free hydroxyl group. "PG(2)-C18 full ester" would therefore describe a polyglycerol fatty acid full ester with the empirical formula $C_{78}O_9H_{150}$ as the major component. In the case of the PG partial ester, the number of fatty acid residues is averaged, whereupon at the same time, the empirical formula provides the fraction with the esterification variation which is present in the majority. A more precise designation of the polyglycerol fatty acid partial ester is provided by additionally providing the hydroxyl value, which is a measure of the non-esterified hydroxyl group content and thus provides information regarding the degree of esterification of the partial ester. Presumably for steric reasons, the esterification reactions in this case occur preferentially from the outside to the inside. Thus, initially, the hydroxyl groups which are esterified are those which allow the fatty acid residue the highest degree of freedom. The first esterification reaction at a linear polyglycerol then preferentially takes place at the hydroxyl group of a first carbon atom of a marginal polyglyceryl unit, then the second esterification reaction takes place at a hydroxyl group of the third carbon atom of the marginal polyglyceryl unit at the other end. Next, the hydroxyl groups at carbon atom positions immediately adjacent to positions which have already been esterified are esterified, and so on.

The term "fatty acids" as used here should be understood to mean aliphatic monocarboxylic acids containing 6 to 22 carbon atoms, which are preferably unbranched and saturated and have an even number of carbon atoms, but they may also contain an odd number, or be branched and/or unsaturated. Preferably, for the esterification of the PGFEs used as the major component of the additive, fatty acids which are saturated and/or unbranched are used. More advantageously, unbranched, saturated fatty acids containing 16, 18, 20 or 22 C atoms are used for the esterification, i.e. palmitic, stearic, arachidic or behenic acid.

Advantageously, the PGFEs of this type which are of use are those which, when the PGFEs or individual PGFE is/are investigated using heat flux differential scanning calorimetry, during the investigation, upon heating up, have only one endothermic minimum and upon cooling down, has only one exothermic maximum, because longer storage periods, raised temperatures or the input of energy via shear forces upon application may arise, which could lead to polymorphic transformation of unsuitable components of the carrier particles and to properties of a corresponding inhalation preparation which are difficult to control. Additional polymorphic forms would be able to be distinguished upon investigation using differential scanning calorimetry by the appearance of a local exothermic maximum upon heating the sample up, as well as a local endothermic minimum upon cooling the sample down. The "blooming" that occurs after some time in storage in which the polymorphism of a component causes a substantial increase in volume which is macroscopically visible, can be avoided by using carrier particle components which exhibit no polymorphism. In particular, triglycerides such as glycerol tripalmitate or glycerol tristearate may have polymorphisms, i.e. respectively both a crystalline unstable a-modification as well as a metastable b'-modification or a stable b-modification may be present and transform from one into the other modification. In this regard, the modifications differ in particular in the thickness of the lamellar, packed crystalline subunits which are also described as subcellular units. As an example, for the a-modification of glycerol tristearate, under specific conditions, stacking of an average of 6 lamellar structures per subcellular unit could be detected and after complete transformation into the b-modification, stacking of an average of 10.5 lamellar structures per subcellular unit and an increase in the crystal thickness of approximately 67% was observed. Because in this case, the computed expected increase of 75% is not obtained, this is presumed to be due to the fact that the individual lamellae of the b-modification have a denser lamellar packing because of the inclined position compared with the a-modification (see D G Lopes, K Becker, M Stehr, D Lochmann et al., in the Journal of Pharmaceutical Sciences 104: 4257-4265, 2015). Denser lamellar packing of this type could then lead to the aforementioned unwelcome ejection of the adhered or encapsulated active ingredient.

Because the carrier particle components are present in the final product, it is also advantageous for the PGFEs which are used to have a stable subcellular form below their solidification temperature at 40° C. and 75% relative humidity for at least 6 months, i.e. under the storage conditions for an accelerated stability test, an essentially constant thickness of the lamellar-structured crystallites evaluated by employing small angle X ray scattering, abbreviated to SAXS, and applying the Scherrer equation. SAXS enables conclusions to be drawn regarding the size, the shape and the internal surfaces of crystallites. The thickness of the respective crystallites can be calculated here using the Scherrer equation, which is $D = K\lambda / FWHM \cos(\theta)$. Here, D designates the thickness of the crystallites and K the dimensionless Scherrer constant, which enables the shape of the crystallites to be predicted and as a rule, to a good approximation, it can be taken to be 0.9. FWHM stands for "full width at half maximum", i.e. the width of the peak of an intensity maximum at half the height above the background, measured in radians, and $\theta$ is the Bragg angle, i.e. the angle of incidence of radiation onto the lattice plane. While a sample of glycerol tripalmitate stabilized with 10% polysorbate 65 has a crystallite thickness of 31 nm after storage for six months at room temperature, corresponding to seven lamellae, and the crystallite thickness after storage for six months at 40° C. is 52 nm, corresponding to 12 lamellae, is almost double, the aforementioned polyglycerol fatty acid esters usually exhibit crystallite thicknesses of 20 to 30 nm, corresponding to 2 to 4 lamellae, and are stable after six months storage at 40° C., with the modifications unchanged. In contrast, polyglycerol full esters usually exhibit a slightly higher crystallite thickness of 30 to 40 nm, indicating a higher degree of organisation, corresponding to 5 to 8 lamellae, and are also stable with unchanged modifications under the storage conditions of an accelerated stability test.

It is also advantageous if, when the PGFEs are used under the stated conditions, the lamellar separation according to an evaluation of the Bragg angle using wide angle X ray scattering, abbreviated to "WAXS", is substantially constant. Individual investigations of the proposed polyglycerol fatty acid esters below their respective solidification temperature using WAXS exhibit one maximum intensity for all polyglycerol fatty acid esters which have been investigated, which means that a respective deflection angle of 21.4°, corresponding to approximately 2θ, i.e. double the Bragg angle, can be deduced, which gives a separation of the lattice planes of 415 pm, which correlates here with the lamellar packing density of the molecules under investigation. This distance can be structurally associated with the a-modification in which the respective lamellar structures are disposed in a hexagonal lattice parallel to each other with molecules stacked on each other and forming planes. Other modifications cannot be identified. The stability of the identified a-modifications was observed both at room temperature and also at 40° C. for 6 months, also using WAXS. Here again, surprisingly, exclusively the respective polyglycerol fatty acid esters under investigation exhibited stable a-modifications.

For the preparation of the additives, PGFEs from the following group are preferably selected: PG(2)-C18 full esters, PG(2)-C22 partial esters with a hydroxyl value of 15 to 100, PG(2)-C22 full esters, PG(3)-C16/C18 partial esters with a hydroxyl value of 100 to 200, PG(3)-C22 partial esters with a hydroxyl value of 100 to 200, PG(3)-C22 full esters, PG(4)-C16 partial esters with a hydroxyl value of 150 to 250, PG(4)-C16 full esters, PG(4)-C16/C18 partial esters with a hydroxyl value of 150 to 250, PG(4)-C16/C18 full esters, PG(4)-C18 partial esters with a hydroxyl value of 100 to 200, PG(4)-C22 partial esters with a hydroxyl value of 100 to 200, PG(6)-C16/C18 partial esters with a hydroxyl value of 200 to 300, PG(6)-C16/C18 full esters, PG(6)-C18 partial esters with a hydroxyl value of 100 to 200, wherein in the polyglycerol fatty acid esters containing two fatty acid residues which are different because of the number of their carbon atoms, those with a lower number are present in an amount of 35% to 45%, those with a corresponding, complementary higher number are present in an amount of 55% to 65% and the specified full esters preferably have a hydroxyl value of less than 5.

An advantageous property of the PGFEs for lipophilic carrier particles in accordance with claim 1 which should be considered is the hydrophobicity, which can be determined by determining the contact angle. The determination of the hydrophobicity is carried out by determining the contact angle between the PGFE in the solid physical state and a droplet of purified water. According to Young's equation, $\cos\theta=(\gamma_{SV}-\gamma_{SL})/\gamma_{LV}$, wherein $\gamma_{SL}$ is the interfacial tension between the PGFE and water, $\gamma_{LV}$ is the interfacial tension of the water droplet and $\gamma_{SV}$ is the surface tension between the PGFE and the surrounding air. θ is the contact angle. Thus, the larger the contact angle θ, the higher is the surface tension between the PGFE and the water and the higher is the hydrophobicity of the PGFE under investigation. The contact angles for the proposed polyglycerol fatty acid esters also correlate with the HLB value which is often used in pharmaceutical technology, which is on a scale of 0 to 20 and provides information regarding the ratio of lipophilic to hydrophilic molecular fractions, wherein the hydrophilic fraction increases with increasing HLB value. For the compression of a powder comprising one or more pharmaceutical substances, the contact angle of the PGFEs used for the lipophilic carrier particles under storage conditions should undergo only moderate changes for the preparation of carrier particles containing one or more pharmaceutical active ingredients, so that the stability of the release kinetics of the pharmaceutical substance or substances from the finished carrier particles is not compromised. Thus, preferably, those polyglycerol fatty acid esters which have a contact angle with water at 40° C. and also at 20° C. after 16 weeks which deviates by less than 10° from the starting value are preferably used as the major component of the carrier particles. As an example, glycerol tristearate has a comparatively high contact angle deviation with water of 40° under the stated conditions and therefore deviates from the desired release kinetics stability; this can be attributed to a transformation from the a- into the b-modification during storage. The solidification temperature for the PGFEs used as additives is preferably below 75° C., but above 40° C. Here, the solidification temperature is defined as the value for the temperature at which the maximum of the highest exothermic peak of the heat flux occurs during analysis of a sample using differential scanning calorimetry.

Because of the conditions for their synthesis, PGFEs are always mixtures of different molecules, in particular in the case of partial esters. It is, however, also possible for a suitable carrier particle in accordance with claim 1 to be provided after synthesis by mixing those PGFEs which can respectively be obtained by esterification reactions which are different because different reaction partners or different reaction conditions are employed.

The term "active ingredient" as used here should be understood to mean a pharmaceutical or cosmetic active ingredient. The term "pharmaceutical active ingredient" as used here should be understood to mean a substance which can be used as the pharmacologically active component of a pharmaceutical. "Substances" here are chemical elements and chemical compounds as well as their naturally occurring mixtures and solutions, plants, plant parts, plant components, algae, fungi and lichens in the processed or unprocessed state, animal bodies, even living animals, as well as human or animal body parts, bodily components and metabolic products in the processed or unprocessed state, microorganisms including viruses as well as their components or metabolic products. "Pharmaceuticals" here are substances or preparations from substances which are specifically for use in or on the human or animal body and are intended for use as agents with healing or alleviating properties or for the prevention of human or animal diseases or disease-causing complaints, or which can be used on the human or animal body or can be administered to a human or to an animal, in order either to restore, correct or influence the physiological functions by a pharmacological, immunological or metabolic effects or to establish a medical diagnosis. "Pharmaceuticals" as used here also encompasses items which contain a pharmaceutical in the aforementioned context or to which a pharmaceutical with the aforementioned meaning is applied and which is therefore to be brought into permanent or temporary contact with the human or animal body, as well as substances and preparations from substances which, in addition in cooperation with other substances or preparations from substances, are intended, without being used on or in the animal body, to detect the condition, status or function of the animal body or to detect pathogens in animals. A cosmetic active ingredient is a substance or a mixture of substances to which a health-promoting or health-sustaining action can be attributed upon application to the skin, intended for the skin or skin appendages such as the hair and nails; examples are hyaluronic acid, collagen, dexpanthenol, aloe vera extract, allantoin or bisabolol, for which, however, a pharmacological action does not necessarily have to have been scientifically proven.

The carrier particles which are provided fulfil their purpose when they are loaded with an active ingredient, in particular a pharmaceutical active ingredient. This may, for example, be carried out by means of a spray drying process in accordance with claim 22, in which the active ingredient and the PGFE or PGFEs are initially dissolved and/or suspended in a suitable organic solvent and then are separated from the solvent once more by spray drying. Examples of suitable solvents are the ether tetrahydrofuran, the alcohol ethanol, the ketone acetone, the ester ethyl acetate or the alkane heptane. It has been shown that by means of spray drying, loading with a pharmaceutical active ingredient of up to 30% by weight is possible.

A further suitable process for the production of the carrier particles in the context of which the carrier particles are loaded with a pharmaceutical active ingredient, is high pressure homogenization in which a mixture of PGFEs or a PGFE mixture is initially produced with water by stirring at a temperature above the melting temperature of the PGFEs or the PGFE mixture, to which the desired pharmaceutical active ingredients and, if necessary and in addition, a nonionic surfactant are added. The mixture is then forced under high pressure of 100 to 2000 bar through a homogenization nozzle, caught and as a rule undergoes this procedure multiple times until the desired droplet size of the lipid phase of an O/W emulsion is obtained, and then is transformed into a suspension of carrier particles loaded with active ingredient in water by cooling.

The PGFEs for which the production of the lipophilic carrier particles are used should be in the solid physical state at least at temperatures of 40° C. or below, so that the carrier particles which are formed can be in the solid form at the same temperatures. During loading with pharmaceutical active ingredients, therefore, care should be taken that a eutectic mixture can be formed with the pharmaceutical active ingredient or active ingredients, which then also should be in the solid state at 40° C. or below. This is also the case for the addition of emulsifiers such as nonionic surfactants but which depends on the active ingredient.

For the pulmonary application of pharmaceutical active ingredients, it has been shown to be advantageous for the carrier particles for the active ingredients to have a mass median aerodynamic diameter (MMAD) of 0.5 μm to 5 μm. The determination of the theoretical MMAD can be computed from the tamped density, the geometrical diameter, determined by light diffraction, and the form factor, determined by polarisation microscopy. It has been shown that carrier particles with MMADs of 0.5 μm and 5 μm can be produced from the PGFEs in particular when the tamped density is less than 0.4 g/cm$^3$.

In respect of the storage properties of the carrier particles, advantageously, they have a water content of less than 2.5%, determined by means of a Karl Fischer titration.

In respect of loading the carrier particles with glucosteroids, such as dexamethasone, for example, the carrier particles also advantageously contain an emulsifier, preferably a nonionic surfactant, in addition to polyglycerol fatty acid esters. In particular, the combination of PG(2)-C18 full ester with poloxamer 188 results in a good encapsulation efficiency for dexamethasone.

Depending on the active ingredient with which the carrier particles are to be loaded, it may also be of advantage to its encapsulation efficiency if the PGFEs are admixed with liquid lipids, wherein, however, the amount of admixture should be kept low so as to keep the carrier particles in the solid state. Furthermore, in the field of cosmetic active ingredients as well, it may be of advantage to dissolve them initially in liquid lipids such as fat-soluble vitamins, for example.

Lipophilic carrier particles in accordance with claim 1 can advantageously be loaded with pharmaceutical active ingredients from the group formed by non-steroidal antirheumatic agents. In this regard, production by spray drying processes according to claim 22 have proved useful, whereupon loading of the carrier particles with up to 30% by weight with the active ingredient ibuprofen could be obtained.

Loading with pharmaceutical active ingredients from the group formed by glucosteroids, on the other hand, is more advantageous using the high pressure homogenisation process. For dexamethasone, for example, an encapsulation efficiency for the carrier particles in aqueous suspension of more than 90% by weight can be obtained.

For the pulmonary application of the carrier particles, whether or not they are loaded with active ingredient, atomizers for the carrier particles suspended in a carrier liquid are available, as well as dosing aerosol nebulizers, in which the carrier particles are dissolved and/or suspended in a propellant and released when a button is pressed, or powder inhalers are available in which the carrier particles are presented in portions so that they can be inhaled when the air stream is inhaled. Irrespective of which device is provided for inhalation of the carrier particles, all variations which comprise such a device and the carrier particles are included under the heading "inhalation preparation".

The invention will now be described in more detail with the aid of examples and figures, without in any way being limited thereto.

EXAMPLE 1

Preparation by Means of Spray Drying Micronized, Lipophilic Carrier Particles Loaded with Ibuprofen for a Powder Inhaler:

A solution of 1.08 g of PG(3)-C22 partial ester-[137], wherein the number in square brackets gives the hydroxyl value, and 0.46 g of ibuprofen was prepared by dissolving the components in 60 g of tetrahydrofuran, in order to subsequently obtain a content of 2.5% by weight of solid. The solution was sprayed in a Procept 4M8-Trix spray dryer in nitrogen, in a closed ring configuration. In this regard, a drying column was used as the drying chamber and a small cyclone separator was used with a pressure difference of 60 mbar. The inlet temperature was set to at least 5° C. above the boiling point of the solvent, and the air flow speed to 0.3 m$^3$/min. The solution was forced through a 0.2 mm bi-fluid nozzle with a nozzle pressure of 0.9 bar at a rate of 3.5 g/min, corresponding to 3 L/min. The separated carrier particles loaded with ibuprofen were removed from the spray drying unit and stored for 10 hours under vacuum in order to remove residual solvent. Carrier particles loaded with 30% by weight ibuprofen with a theoretical MMAD of 4.10 μm were obtained. The bulk density was 0.215 g/cm$^3$, the tamped density was 0.342 g/cm$^3$, the true density was 1.069 g/cm$^3$, and the water content was 0.45%. The differential scanning calorimetry for the eutectic mixture of ibuprofen and PG(3)-C22 partial ester-[137] provided the values listed below.

1) immediately after preparation of the carrier particles loaded with ibuprofen;
2) after storage for one month at 20° C.;
3) after storage for one month at 40° C.:

|  | ad 1) | ad 2) | ad 3) |
|---|---|---|---|
| Start of melting process: | 58.0° C. (± 0.06° C.) | 58.1° C. (± 0.07° C.) | 58.1° C. (± 0.07° C.) |
| Melting temperature: | 60.9° C. (± 0.12° C.) | 60.8° C. (± 0.07° C.) | 60.8° C. (± 0.14° C.) |

|  | ad 1) | ad 2) | ad 3) |
|---|---|---|---|
| Crystallization temperature: | 57.9° C. (± 0.06° C.) | 58.1° C.(± 0.07° C.) | 58.0° C. (± 0.00° C.) |
| Heat of fusion: | 139.2° C. (± 5.1° C.) | 139.2° C. (± 6.2° C.) | 139.8° C. (± 5.4° C.) |

EXAMPLE 2

Figure 11:
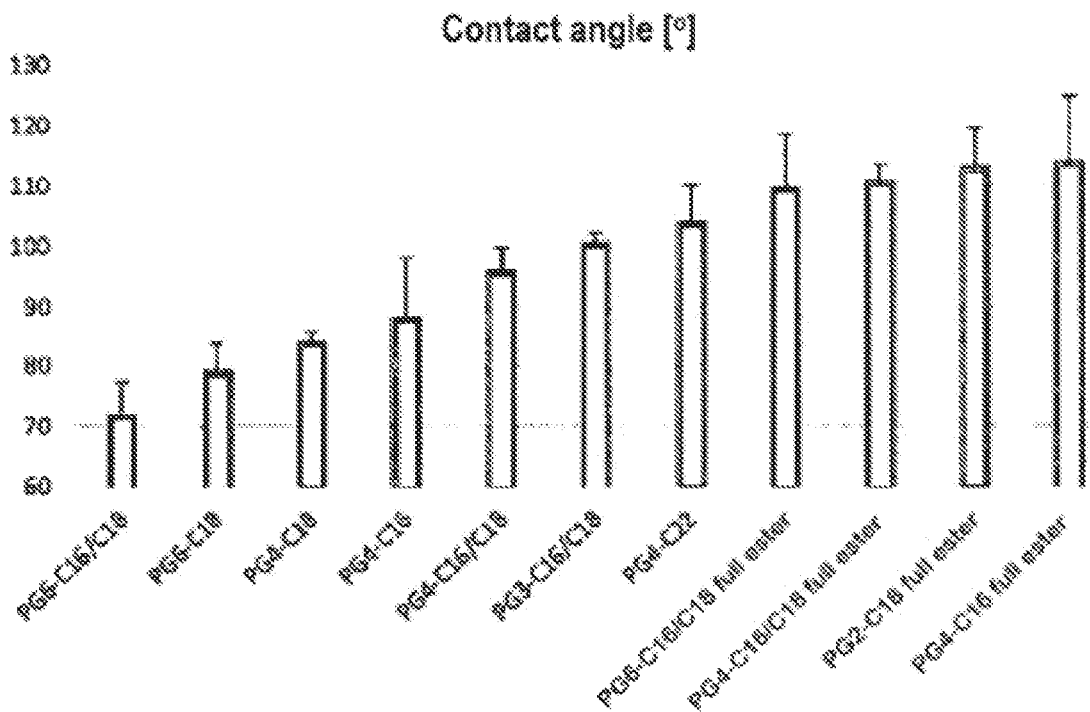
Figure 12:
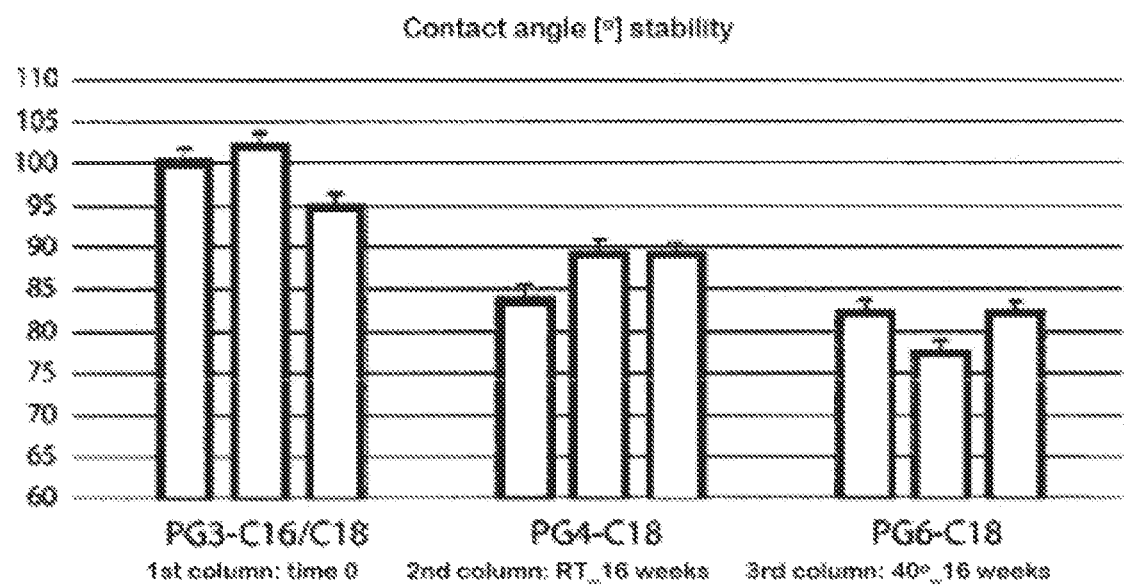

Preparation Using High Pressure Homogenization of Micronized, Lipophilic Carrier Particles Loaded with Dexamethasone as a Suspension for a Nebulizer 0.1% by weight of dexamethasone was added to PG(2)-C18 full ester melted at 70° C. and stirred at 750 revolutions per minute for 60 minutes using a magnetic stirrer to form a clear solution. 100 mL of pre-emulsion for the high pressure homogenization was produced at 70° C. by mixing 10% by weight of the clear solution, 2.5% by weight of poloxamer 188 and 87.5% by weight of purified water with an Ultraturrax T25 (Janke & Kunkel, IKA, Germany) for two minutes at 20500 revolutions per minute. The pre-emulsion underwent high pressure homogenizations in three successive passes which were also carried out at 70° C. In this regard, a Panda K2 NS1001L high pressure homogenizer with a splitting valve (GEA NiroSoavi, Germany) was used. The particle size was determined using a Mastersizer 2000 (Malvern, United Kingdom), which is a tool for analysing the deflection of a laser beam on the basis of random light scattering. 10-30 μL of the suspension to be investigated was added to the measuring cell which already contained 20 mL of highly purified water, in order to obtain a turbidity of between 4% and 6%. The particle fraction index was set to 1.55, and the particle absorption index was set to 0.01 in order to obtain a residual value of less than 1 for each measurement. The pump speed was 1750 revolutions per minute. The data analysis was carried out on the basis of the Mie theory. The median particle size ($d_{50}$) according to this was 212 nm. The differential scanning calorimetry for the nanosuspension compared with the clear solution of PG(2)-C18 full ester and dexamethasone showed that the addition of polyoxamer 188 produced no indication of a polymorphic transformation of the stable crystal modification of the PGFE.

The properties of some PGFEs will now be illustrated by way of example and with the aid of the figures.

The partial ester PG(4)-C18 had the quantitative main structure shown in FIG. 1, when investigated using gas chromatography linked with mass spectroscopy (GC-MS).

FIG. 2 shows the results of the investigation of PG(4)-C18 using differential scanning calorimetry, wherein the temperature values are on the X axis of the diagram and the heat flux in mW/g is on the Y axis. The left hand diagram in FIG. 2 shows two almost coincident curves for two measurements of the partial ester PG(4)-C18, which each exhibit precisely one endothermic minimum which can be assigned to the energy-consuming transition from the solid to the liquid phase upon melting of the partial ester. The right hand diagram for the partial ester PG(4)-C18 in FIG. 2 shows precisely one exothermic maximum which can be assigned to the energy-releasing transition from the liquid to the solid phase upon solidification of the partial ester. The measurements were carried out using a DSC 204 F1 Phoenix from Nietzsch Gerstebau GmbH, 95100 Selb, Germany. In this regard, a sample of 3-4 mg was weighed into an aluminium crucible and the heat flux was continuously recorded at a heating rate of 5K per minute. A second run was carried out using the same heating rate.

FIG. 3 shows, as a contrast to the desired behaviour of the polyglycerol fatty acid ester, the typical behaviour of a polymorphic triacyl glycerol during an investigation using differential scanning calorimetry and upon heating up. Here, two local endothermic minima with an intermediate exothermic maximum can be seen, wherein the first endothermic minimum on the left hand side is due to melting of the unstable a-modification followed by the exothermic maximum upon crystallization to form the more stable b-modification, which in turn melts as the temperature rises further, as can be seen by the second local endothermic minimum on the right hand side.

FIG. 4 shows the PG(4)-C18 partial ester investigated using differential scanning calorimetry upon heating up, after storage for 6 months at room temperature. FIG. 5 shows the PG(4)-C18 partial ester investigated using differential scanning calorimetry, upon heating up after storage for 6 months at 40° C. In both cases, as before, there is no exothermic maximum which could indicate crystallization into a more stable modification.

For the WAXS and the SAXS analyses, a spot focusing camera system, S3-MICRO, formerly Hecus X ray Systems Gesmbh, 8020 Graz, Austria, now Bruker AXS GmbH, 76187 Karlsruhe, Germany, was equipped with two linear position-sensitive detectors with a resolution of 3.3-4.9 Angstroms (WAXS) and 10-1500 Angstroms (SAXS). The samples were introduced into a glass capillary with a diameter of approximately 2 mm, which was then sealed with wax and placed in the rotary capillary unit. The individual measurements were made at room temperature by exposure to a beam of X rays at a wavelength of 1.542 Angstroms for 1300 sec.

FIG. 6 shows the results of the WAXS analysis for different polyglycerol fatty acid esters including PG(4)-C18 partial ester (labelled) below their solidification temperature, which all exhibit an intensity maximum at a 2θ of 21.4°. The Bragg angle corresponds to a separation of the lattice planes of 415 pm, which is typical for the lamellar packing of the a-modification. The maximum intensity was stable both after storage for 6 months at room temperature, as can be seen in FIG. 7, and also after storage for 6 months at 40° C., as can be seen in FIG. 8.

FIG. 9 shows the results of the SAXS analysis for various polyglycerol fatty acid esters. For PG(4)-C18 partial ester, a lamellar separation of 65.2 Angstroms could be derived. The thickness of the crystallites, calculated from the Scherrer equation, was 12.5 nm with a Scherrer constant of 0.9, a wavelength of 1.542 Angstroms, a FWHM value of 0.0111 and a Bragg angle θ of 0.047 (radians). The values for the SAXS analysis of PG(4)-C18 partial ester remained the same even after storage for six months, both at room temperature and also at 40° C. (not shown).

The analysis from the differential scanning calorimetry also enabled predictions to be made about the solidification temperature of the PG(4)-C18 partial ester. The peak of the exothermic maximum upon cooling the sample down was between 53.4° C. and 57.0° C. with the maximum at 55.2° C., which marks the solidification temperature.

FIG. 10 shows a diagram illustrating the measurement of the contact angle (see para [0020]). For PG(4)-C18 partial esters, the contact angle is approximately 84°, which correlates to a HLB value of approximately 5.2. Compared with other polyglycerol fatty acid esters, PG(4)-C18 partial esters can be assigned to the hydrophilic polyglycerol fatty acid esters, as can be seen in FIG. 11 (here=PG4-C18). FIG. 12 shows the variation in contact angle for PG(4)-C18 partial esters, see central graph, against the start measurement (left hand column), after 16 weeks at room temperature (central column) and after 16 weeks at 40° C. (right hand column). The contact angle varied by no more than 10°, and so the hydrophobicity can be described as stable compared with monoglycerol fatty acid esters such as tristearyl glycerol, for example. This is also the case for the PG3-C16/C18 partial ester also shown in FIG. 12, left hand graph, and PG6-C18 partial esters, right hand graph.

The invention claimed is:

1. Lipophilic carrier particles for cosmetic or pharmaceutical active ingredients in producing pulmonary applicable pharmaceuticals, wherein the lipophilic carrier particles have, as main constituent, one or more polyglycerol fatty acid esters which exhibit no polymorphism, each obtained from a complete or partial esterification of a linear or branched polyglycerol having two to eight glyceryl units with one or more fatty acids each being saturated and unbranched and each containing an even number of carbon atoms from 6 to 22, wherein the lipophilic carrier particles have a mass median aerodynamic diameter (MMAD) of 0.5 μm to 5 μm and a tamped density of less than 0.4 g/$cm^3$.

2. Lipophilic carrier particles as claimed in claim 1, characterized in that the one or more fatty acids for the synthesis of the one or more polyglycerol fatty acid esters contain 16, 18, 20 or 22 carbon atoms.

3. Lipophilic carrier particles as claimed in claim 1, characterized in that an investigation of the one or more polyglycerol fatty acid esters using heat flux differential scanning calorimetry produces, upon heating up, respectively only one endothermic minimum and upon cooling down, respectively only one exothermic maximum.

4. Lipophilic carrier particles as claimed in claim 1, characterized in that the one or more polyglycerol fatty acid esters have a stable subcellular form below the solidification temperature with a lamellar separation over at least 6 months at 40° C. which is constant according to an evaluation of the Bragg angle determined by WAXS analysis.

5. Lipophilic carrier particles as claimed in claim 1, characterized in that the one or more polyglycerol fatty acid esters have a stable subcellular form below the solidification temperature with a constant thickness of the lamellar-structured crystallites over at least 6 months at 40° C. according to SAXS analysis evaluated using the Scherrer equation.

6. Lipophilic carrier particles as claimed in claim 1, characterized in that the lipohilic carrier particles comprise at least one polyglycerol fatty acid ester from the following group: PG(2)-C18 full esters, PG(2)-C22 partial esters with a hydroxyl value of 15 to 100, PG(2)-C22 full esters, PG(3)-C16/C18 partial esters with a hydroxyl value of 100 to 200, PG(3)-C22 partial esters with a hydroxyl value of 100 to 200, PG(3)-C22 full esters, PG(4)-C16 partial esters with a hydroxyl value of 150 to 250, PG(4)-C16 full esters, PG(4)-C16/C18 partial esters with a hydroxyl value of 150 to 250, PG(4)-C16/C18 full esters, PG(4)-C18 partial esters with a hydroxyl value of 100 to 200, PG(4)-C22 partial esters with a hydroxyl value of 100 to 200, PG(6)-C16/C18 partial esters with a hydroxyl value of 200 to 300, PG(6)-C16/C18 full esters, PG(6)-C18 partial esters with a hydroxyl value of 100 to 200, wherein in the polyglycerol fatty acid esters containing two fatty acid residues which are different because of the number of their carbon atoms, those with a lower number are present in an amount of 35% to 45%, those with a corresponding, complementary higher number are present in an amount of 55% to 65% and the specified full esters have a hydroxyl value of less than 5.

7. Lipophilic carrier particles as claimed in claim 1, characterized in that the one or more polyglycerol fatty acid esters have a solidification temperature of below 75° C.

8. Lipophilic carrier particles as claimed in claim 1, characterized in that the contact angle of the one or more polyglycerol fatty acid esters during the determination of the hydrophobicity differs by less than 10° from the starting value after 16 weeks at 40° C. as well as at 20° C.

9. Lipophilic carrier particles as claimed in claim 1, characterized in that the lipophilic carrier particles comprise a post-synthesis mixture of the one or more polyglycerol fatty acid esters which are respectively obtained from esterification reactions which are different because different reaction partners are used or because different reaction conditions are employed.

10. Lipophilic carrier particles as claimed in claim 1, characterized in that the lipophilic carrier particles comprise one or more pharmaceutical active ingredients.

11. Lipophilic carrier particles as claimed in claim 10, characterized in that the lipophilic carrier particles have an active ingredient content of more than 10% by weight.

12. Lipophilic carrier particles as claimed in claim 1, characterized in that the lipophilic carrier particles have a solid physical state at temperatures of 40° C. or less.

13. Lipophilic carrier particles as claimed in claim 1, characterized in that the lipophilic carrier particles have a water content of less than 2.5%.

14. Lipophilic carrier particles as claimed in claim 1, characterized in that the lipophilic carrier particles comprise an emulsifier.

15. Lipophilic carrier particles as claimed in claim 1, characterized in that the lipophilic carrier particles comprise one or more incorporated liquid lipids.

16. Lipophilic carrier particles as claimed in claim 1, characterized in that the lipophilic carrier particles comprise at least one pharmaceutical active ingredient from the group consisting of glucosteroids.

17. Lipophilic carrier particles as claimed in claim 1, characterized in that the lipophilic carrier particles comprise at least one pharmaceutical active ingredient from the group consisting of non-steroidal antirheumatic agents (NSAR).

18. A process for the production of the lipophilic carrier particles as claimed in claim 1, characterized by the following steps:

i) dissolving and/or suspending the one or more polyglycerol fatty acid esters in an organic solvent, ii) removing the organic solvent by means of spray drying.

19. The process as claimed in claim 18, characterized in that prior to step ii), at least one pharmaceutical active ingredient is dissolved and/or suspended in the organic solvent.

20. A process for the production of the lipophilic carrier particles as claimed in claim 1, characterized by the following steps:

i) producing a mixture of the one or more polyglycerol fatty acid esters with water by stirring at a temperature which is above the melting temperature of the one or more polyglycerol fatty acid esters, ii) spraying the mixture once or multiple times through a high pressure homogenization nozzle to form an O/W emulsion, iii) cooling the lipid phase to form solid particles in water.

21. The process as claimed in claim 20, characterized in that at least one emulsifier is added to the mixture in step i).

22. The process as claimed in claim 20, characterized in that at least one pharmaceutical active ingredient is added to the mixture in step i).

23. Lipophilic carrier particles as claimed in claim 1, characterized in that the lipophilic carrier particles comprise a nonionic surfactant.

\* \* \* \* \*